(12) United States Patent
Higa et al.

(10) Patent No.: US 6,864,283 B2
(45) Date of Patent: Mar. 8, 2005

(54) OXY-AND AMINO-SUBSTITUTED TETRAHYDROFURYL DERIVATIVES WITH ANTITUMOUR ACTIVITY

(75) Inventors: Tatsuo Higa, Okinawa (JP); Junichi Tanaka, Okinawa (JP); Dolores Garcia Gravalos, Madrid (ES)

(73) Assignee: Pharma Mar, S.A., Madrid (ES)

( * ) Notice: Subject to any disclaimer, the term of this patent is extended or adjusted under 35 U.S.C. 154(b) by 0 days.

(21) Appl. No.: 10/203,918

(22) PCT Filed: Feb. 16, 2001

(86) PCT No.: PCT/GB01/00655

§ 371 (c)(1),
(2), (4) Date: Oct. 10, 2002

(87) PCT Pub. No.: WO01/60810

PCT Pub. Date: Aug. 23, 2001

(65) Prior Publication Data

US 2003/0092738 A1 May 15, 2003

(30) Foreign Application Priority Data

Feb. 16, 2000 (GB) .............................................. 0003629
Sep. 5, 2000 (GB) .............................................. 0021774

(51) Int. Cl.[7] ...................... A61K 31/34; C07D 307/02; C07F 4/28
(52) U.S. Cl. ...................... 514/472; 514/473; 549/475; 549/476; 549/480; 549/216; 549/218
(58) Field of Search ................................. 514/472, 473; 549/475, 476, 480, 216, 218

(56) References Cited

FOREIGN PATENT DOCUMENTS

| EP | 0381 514 A2 | 8/1990 |
|---|---|---|
| WO | WO 01/60810 A 1 | 8/2001 |

OTHER PUBLICATIONS

ApSumon et al., J. Ame. Chem. Soc. Chem. Commu. (1965), pp. 4164–4168.*
Sugiyama et al., Liebigs Ann. Chem. (1990), pp. 1069–1078.*
Bink et al., Liebigs Ann. Chem. (1993), pp. 71–75.*

(List continued on next page.)

*Primary Examiner*—Deborah C. Lambkin
(74) *Attorney, Agent, or Firm*—Fish & Richardson, P.C.

(57) ABSTRACT

Compounds of formula (I) wherein $R_1$ is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl; or $R_1$ together with $R_2$ forms a saturated or unsaturated heterocyclic ring; $R_2$ and $R_3$ are each, independently, selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl; or one of $R_2$ or $R_3$ together with $R_1$ forms a saturated or unsaturated heterocyclic ring; or $R_2$ and $R_3$ together form a saturated or unsaturated heterocyclic ring; $R_4$ is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl, wherein R' is selected from the group consisting of H, OH, $NO_2$, $NH_2$, SH, CN, halogen, C(=O)H, C(=O)$CH_3$, $CO_2$H, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted and unsubstituted aryl; R" is selected from the group consisting of H, OH, $NO_2$, $NH_2$, SH, CN, halogen, =O, C(=O)H, C(=O)$CH_3$, $CO_2$H, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted and unsubstituted aryl; wherein $X_1$, $X_2$ $X_3$ on formula I are independently placed in any particular position of the chain and independently selected from H, OH, OR', SH, SR', SOR', $SO_2$R', $NO_2$, $NH_2$, NHR', N(R')$_2$, NHC(O)R', CN, halogen, =O, C(=O)H, C(=O)$CH_3$, $CO_2$H, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic, wherein substituent groups defined by R' are each independently selected from the group consisting of H, OH, OR', SH, SR', SOR', $SO_2$R', $NO_2$, $NH_2$, NHR', N(R')$_2$, NHC(O)R', CN, halogen, =O, C(=O)H, C(=O)$CH_3$, $CO_2$H, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, and substituted or unsubstituted heteroaromatic; wherein x is 6 to 20; and wherein the dotted lined is one or several optional double bonds placed in any particular position of the side chain; or pharmaceutically acceptable salts thereof are useful as antitumor compounds and include compound IK-8-73-4 of structure (a) which was isolated from a sponge *Pachastrissa* sp.

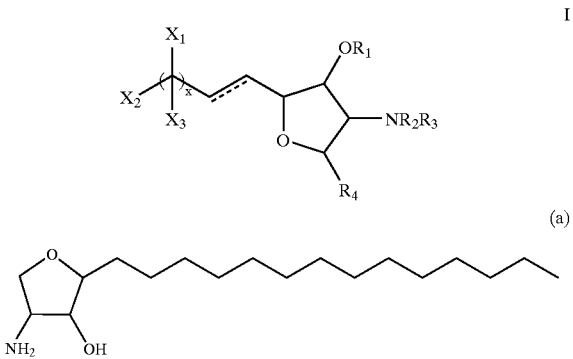

10 Claims, No Drawings

OTHER PUBLICATIONS

J.W. Apsimon et al.: "The chemistry of fungi" Journal of the Chemical Society, Chemical Communications., 1965, pp. 4164–4168.

Birk, Rolf et al., "Epoxides of phytosphingosine and derivatives, potential inhibitors of sphingosine biosynthesis" Liebigs Ann. Chem., (1993), (1), 71–75.

Kishimoto, Yasuo et al: "Anhydrocerebrin from baker's yeast. Further confirmation of its structure and unusual opening of its tetrahydrofuran ring" Biochemistry (1974), 13(19), 3992–3999.

Chemical Abstracts, vol. 54, No. 19, Oct. 10, 1960 Columbus, Ohio, US; abstract No. 19513h, M. Prostenik et al.: "The sphingolipide series. XII. Structure of the cerebrin anyhdro base of yeast".

Chemical Abstracts, vol. 54, No. 19,, Oct. 10, 1960 Columbus, Ohio, US; abstract No. 19514c, M. Prostenik et al.: "XIII. The ceramides and ceramide esters of C20–phytosphingosine and C20–phytosphingosine anhydro base of yeast".

Chemical Abstracts, vol. 55, No. 23, Nov. 13, 1961 Columbus, Ohio, US; abstract No. 23358a, M. Prostenik et al.: "Sphingolipide series XV. Partial Synthesis of anyhdro cerebrin of yeast".

Prostenik et al., "Studies in the Sphingolipids Series. XII. Structure of the Cerebrin Anhydro Base of Yeast (C20–Phytosphingosine Anhydro Base)", Croat. Chem. Acta, vol. 32, No. 1, pp. 11–15 (1960).

Prostenik et al., "Studies in the Sphingolipids Series, XV. Partial Synthesis of Anhydro Cerebrin of Yeast", Croat. Chem. Acta., vol. 32, No. 3, pp. 133–138 (1960).

Ries–Lesic et al., "Studies in Sphingolipids Series. XIII. On the Ceramides and Ceramide Esters of C20–Phytosphingosine and C20–Phytosphingosine Anhydro Base of Yeast", Croat. Chem. Acta., vol. 32, No. 11, pp. 17–21 (1960).

Sugiyama, Shigeo et al., "Biologically active glycosides from Asteroidea. XXIV. Stereocehmistry o the four diastereomers of phytosphingosine", Liebigs Ann. Chem. (1990), (11), 1069–1078.

Sugiyama, Shigeo et al., "Biologically active glycosides from asteroidean. XV. Asymmetric synthesi of phytosphingosine and phytosphingosine anhydro base. Assignment of the absolute stereochemistry", Liebigs Ann. Chem. (1988), (7), 619–625.

* cited by examiner

OXY- AND AMINO-SUBSTITUTED TETRAHYDROFURYL DERIVATIVES WITH ANTITUMOUR ACTIVITY

CROSS-REFERENCE TO RELATED APPLICATIONS

This application is a 35 U.S.C. §371 National Phase filing of PCT Application No. PCT/GB01/00655 filed Feb. 16, 2001, which application claimed priority under each of the following commonly owned British Patent Applications-No. 0003629.3, filed Feb. 16, 2000; No. 0021774.5, filed Sep. 5, 2000. The PCT application designated the United States and was published in the English language on Aug. 23, 2001 as WO 01/60810.

The Present Invention Relates to Antitumour Compounds.

BACKGROUND OF THE INVENTION

Marine organisms continue to be an interesting source of biologically active molecules. Compounds such as ecteinascidin 743 are in clinical trials. Some important active compounds have been isolated from sponges, notably palau'amine. Other compounds of marine origin include spisulosines such as spisulosine 285 which is of interest for its antitumor activity, and reference is made to WO 9952521.

SUMMARY OF THE INVENTION

The present invention is directed to compounds which are analogs of the spisulosine family, having the following formula I:

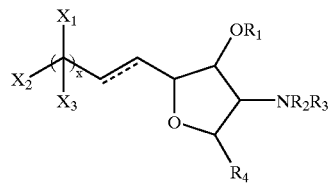

wherein the substituent groups defined by $R_1$, $R_2$, $R_3$ and $R_4$ are each independently selected of H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl. Wherein each of the R', R" groups is independently selected from the group consisting of H, OH, $NO_2$, $NH_2$, SH, CN, halogen, =O, C(=O)H, C(=O)$CH_3$, $CO_2$H, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl. Wherein $R_1$, $R_2$, $R_3$ could form part of a heterocyclic ring (saturated: e.g. morpholine, oxazolidine or containing unsaturated double bonds: e.g. morpholinone, oxazolidinone, typically having 5 or 6 ring atoms). $R_2$ can be independently an internal salt. Wherein $X_1$, $X_2$ and $X_3$ on formula I are independently placed in any particular position of the chain including closer to the ring on either carbon with the dotted line and independently selected of H, OH, OR', SH, SR', SOR', $SO_2R'$, $NO_2$, $NH_2$, NHR', $N(R')_2$, NHC(O)R', CN, halogen, =O, C(=O)H, C(=O)$CH_3$, $CO_2$H, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic. Wherein substituent groups defined by R' are each independently selected from the group consisting of H, OH, OR', SH, SR', SOR', $SO_2R'$, $NO_2$, $NH_2$, NHR', $N(R')_2$, NHC(O)R', CN, halogen, =O, C(=O)H, C(=O)$CH_3$, $CO_2$H, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic.

Wherein x can be between 6 and 20.

Wherein the dotted line is one or several double bonds placed in any particular position of the side chain.

Wherein the stereochemistry of the groups $OR_1$ and $NR_2R_3$ can be independently syn or anti.

Antitumoral activities of these compounds include leukaemias, lung cancer, colon cancer, kidney cancer, prostate cancer, ovarian cancer, breast cancer, sarcomas and melanomas.

The compounds are of thus of use in medicine, in particular in the treatment of tumours. The invention also relates to pharmaceutical preparations comprising such compounds for treatment of tumours, for example, solid tumours, and use of the compounds in the preparation of a medicament for the treatment of tumours.

In particular, we provide the compound we designate IK-8-73-4. The compound IK-8-73-4 is of formula $C_{18}H_{37}NO_2$ and has the structure:

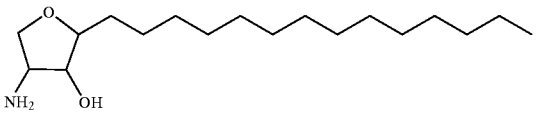

The compounds of this invention can form salts, for example $R^2$ can be independently an internal salt. Preferred internal salts are formed using any kind of mineral or organic acid such as hydrochloric acid, hydrobromic acid, tartaric acid, succinic acid, etc. The method, use and compositions of this invention extend to such pharmaceutically acceptable salts.

PREFERRED EMBODIMENTS

In some preferred compounds, the group $R_4$ is hydrogen. One or both of $R_2$ and $R_3$ is suitably hydrogen. Typically $R_1$ is hydrogen. Preferably one, two or three of $X_1$, $X_2$ and $X_3$ are hydrogen. Suitably the dotted line is absent to leave a single bond. Preferably x is 10 to 18, more preferably 10 to 14, such as about 12.

Suitable halogen substituents in the compounds of the present invention include F, Cl, Br and I.

Except where indicated, alkyl groups preferably have from 1 to about 12 carbon atoms, more preferably 1 to about 8 carbon atoms, still more preferably 1 to about 6 carbon atoms, and most preferably 1, 2, 3 or 4 carbon atoms. Methyl, ethyl and propyl including isopropyl are particularly preferred alkyl groups in the compounds of the present invention. As used herein, the term alkyl, unless otherwise modified, refers to both cyclic and noncyclic groups, although cyclic groups will comprise at least three carbon ring members.

Preferred alkenyl and alkynyl groups in the compounds of the present invention have one or more unsaturated linkages and from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred.

Preferred alkoxy groups in the compounds of the present invention include groups having one or more oxygen linkages and from 1 to about 12 carbon atoms, more preferably from 1 to about 8 carbon atoms, and still more preferably 1 to about 6 carbon atoms, and most preferably 1, 2, 3 or 4 carbon atoms.

Preferred alkylthio groups in the compounds of the present invention have one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred.

Preferred alkylsulfinyl groups in the compounds of the present invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2 3 or 4 carbon atoms are particularly preferred.

Preferred alkylsulfonyl groups in the compounds of the present invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred.

Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties.

Suitable heteroaromatic groups in the compounds of the present invention contain one, two or three heteroatoms selected from N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, imidazolyl, indolyl, benzofuranyl and benzothiazolyl. Suitable heteroalicyclic groups in the compounds of the present invention contain one, two or three heteroatoms selected from N, O or S atoms and include, e.g., tetrahydrofuranyl, tetrahydropyranyl, piperidinyl, morpholino and pyrrolindinyl groups.

Suitable carbocyclic aryl groups in the compounds of the present invention include single and multiple ring compounds, including multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl including substituted phenyl such as 2-substituted phenyl, 3-substituted phenyl, 2,3-substituted phenyl, 2,5-substituted phenyl, 2,3,5-substituted and 2,4,5-substituted phenyl, including where one or more of the phenyl substituents is an electron-withdrawing group such as halogen, cyano, nitro, alkanoyl, sulfinyl, sulfonyl and the like; naphthyl including 1-naphthyl and 2-naphthyl; biphenyl; phenanthryl; and anthracyl.

References herein to substituted R' groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a fluoro, chloro, bromo and iodo: cyano; hydroxyl; nitro; azido; alkanoyl such as a $C_{1-6}$ alkanoyl group such as acyl and the like; carboxamido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl (e.g., R being a substituted or unsubstituted biphenyl moiety); and aralkyl such as benzyl.

Similar considerations apply to the substituted groups permitted for $X_1$, $X_2$ and $X_3$, including substituted $C_1$–$C_{18}$ alkyl, substituted $C_2$–$C_{18}$ alkenyl, substituted $C_2$–$C_{18}$ alkynyl, substituted aryl, substituted heteroaromatic, as well as for these groups where mentioned for R'. Preferably these definitions are interpreted to avoid unmeaningful multiple substitutions, such as alkyl substituted by alkyl, which remains an alkyl group, as well as to avoid structures which are not credible for the purpose of this invention. Preferably there are at most 10 to 50, more preferably 12 to 40, 14 to 30 or most preferably 16 to 20 carbon atoms in the molecule.

The substituents $X_1$, $X_2$ and $X_3$ on formula I are independently placed in any particular position of the chain including closer to the ring on either carbon with the dotted line and independently selected. Thus, for example, there may be a substituent adjacent the ring, another further from the ring, and another remote from the ring.

Preferred internal salts are formed using any kind of mineral or organic acid such as hydrochloric acid, hydrobromic acid, tartaric acid, succinic acid, etc.

In a preferred class of compounds of this invention, $R_4$ is an alkyl chain with a substituent —$NR^2R^3$ and a substituent —$YR^1$ or =$YR^1$ on the next carbon towards the furan ring, where Y is selected from the group consisting of N, O, P, S and is preferably O. Suitably the amino group is on the second carbon and the amino group on the third carbon, counting the terminal carbon as the first.

There can be unsaturation in the —$(CH_2)_n$—, preferably a single unsaturation.

Preferred compounds of this invention include as side chain the partial structure:

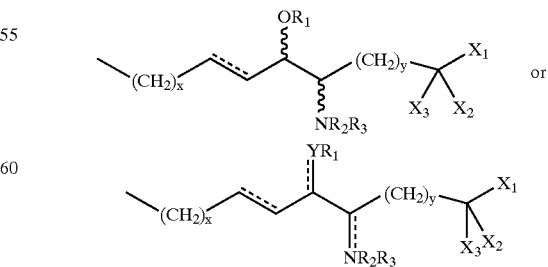

Where the dotted line is a single or double bond. Wherein $X_1$, $X_2$ and $X_3$ on formula I and formula II are independently selected of H, OH, OR', SH, SR', SOR', SO$_2$R', NO$_2$, NH$_2$, NHR', N(R')$_2$, NHC(O)R', CN, halogen, =O, C(=O)H, C(=O)CH$_3$, CO$_2$H, CO$_2$CH$_3$, substituted or unsubstituted C$_1$–C$_{18}$ alkyl, substituted or unsubstituted C$_2$–C$_{18}$ alkenyl, substituted or unsubstituted C$_2$–C$_{18}$ alkynyl, substituted or unsubstituted aryl, substituted or unsubstituted heteroaromatic. Wherein x and y can be between 0 and 20. Preferably x is in the range 8 to 16, more preferably 10, 11, 12, 13 or 14. Preferably y is 0, 1 or 2. Currently the most preferred is that x is 11, 12 or 13, and y is 0 or 1.

The compound IK-8-73-4 can isolated from the sponge *Pachastrissa* sp, Desmospongiae, Astrophorida, Calthropellidae. Accordingly, the invention also relates to compound IK-8-73-4 obtainable from *Pachastrissa* sp., and to a method of isolating IK-8-73-4, characterised in that the starting material for the isolation is *Pachastrissa* sp.

The compound isolated from the sponge exists in the following stereochemistry:

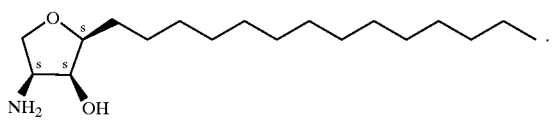

The biological activity of the compound is illustrated by the following IC50 data, μg/ml:

| P$_3$88 | A$_{459}$ | HT$_{29}$ | MEL$_{28}$ |
| --- | --- | --- | --- |
| leukemia | human lung | human colon | melanoma |
| 0.01 | 0.01 | 0.01 | 0.01 |

Another especially preferred embodiment of the present invention is pharmaceutical compositions useful as antitumor agents which contain as active ingredient a compound or compounds of the invention, as well as the processes for their preparation.

Examples of pharmaceutical compositions include any solid (tablets, pills, capsules, granules etc.) or liquid (solutions, suspensions or emulsions) with suitable composition or oral, topical or parenteral administration.

Administration of the compounds or compositions of the present invention may be any suitable method, such as intravenous infusion, oral preparation, intraperitoneal and intravenous preparation.

The compounds of this invention can also be made by synthesis. Illustratively, the compounds can be made having regard to the procedure in Scheme 6 of Liebigs Ann. Chem., 1990, 1069–1078. In Scheme 6, (2R,3S,4S)-4-benzoylamido-3-hydroxy-2-dodecyltetrahydrofuran, compound 43, is prepared from (4S, 1'S, 2'R-4,5-dihydro-4-(1', 2'-dihydroxytetradecy)-2-phenyl-1,3-oxazole, compound 35. The (2R, 3S, 4S)-4-benzoylamido-3-hydroxy-2-dodecyltetrahydrofuran is then converted through (2R, 3S, 4S)-4-benzylamido-3-hydroxy-2-dodecyltetrahydrofuran and (2R,3S,4S)-4-amino-3-hydroxy-2-dodecyltetrahydrofuran to give (2R, 3S, 4S)-4-acetamido-3-acetoxy-2-dodecyltetrahydrofuran, compound 45. The 4-benzylamido-3-hydroxy-2-dodecyltetrahydrofuran and (2R, 3S, 4S)-4-amino-3-hydroxy-2-dodecyltetrahydrofuran are intermediates and are not purified.

This procedure can be used to prepare further compounds of this invention, by modifying as necessary the starting material 35 or 43 in Scheme 6, and isolating the debenzylated compound obtained at the end of the second step in the transition from compound 43 to compound 45, followed by derivatisation as necessary. Moreover, other procedures are available for the synthesis of tetrahydrofurans, and they can be adjusted as appropriate to give compounds of this invention.

The synthetic compounds of this invention are preferably provided in substantially pure form, that is free from impurity including starting material and reagents. In particular, we provide the benzyl and debenzylated compound obtained at the end of the first and second steps in the transition from compound 43 to compound 45 of the procedure in Liebigs Ann. Chem., 1990, 1069–1078. The invention extends to compositions and use of the benzoyl and acetyl compounds, compounds 43 and 45.

Examples of pharmaceutical compositions of the invention include any solid (for example tablets, pills, capsules, granules) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

Suitably, the compound may be conjugated to a carrier protein or another suitable agent for delivery into the animal or human body. Conjugation may occur directly between a carrier and the compound, or indirectly via a suitable linker.

Administration of the compound or compositions of the present invention may be by any suitable method, such as intravenous infusion, oral preparations, intraperitoneal and intravenous administration. We prefer that infusion times of up to 24 hours are used, more preferably 2–12 hours, with 2–6 hours most preferred. Short infusion times which allow treatment to be carried out without an overnight stay in hospital are especially desirable. However, infusion may be 12 to 24 hours or even longer if required. Infusion may be carried out at suitable intervals of say 2 to 4 weeks. Pharmaceutical compositions containing compound of the invention may be delivered by liposome or nanosphere encapsulation, in sustained release formulations or by other standard delivery means.

The correct dosage of the compound will vary according to the particular formulation, the mode of application, and the particular situs, host and cancer or tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compound of this invention may be used with other drugs to provide a combination therapy. The other drugs may form part of the same composition, or be provided as a separate composition for administration at the same time or a different time. The identity of the other drug is not particularly limited, and suitable candidates include:

a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);

b) antimetabolite drugs such as 5-fluorouracil, cytarabine, gemcitabine, purine analogues such as pentostatin, methotrexate);

c) alkylating agents such as nitrogen mustards (such as cyclophosphamide or ifosphamide);

d) drugs which target DNA such as the antracycline drugs adriamycin, doxorubicin, pharmorubicin or epirubicin;

e) drugs which target such as etoposide;

f) hormones and hormone agonists or antagonists such as estrogens, antiestrogens (tamoxifen and related compounds) and androgens, flutamide, leuprorelin, goserelin, cyprotrone or octreotide;

g) drugs which target signal transduction in tumour cells including antibody derivatives such as herceptin;

h) alkylating drugs such as platinum drugs (cis-platin, carbonplatin, oxaliplatin, paraplatin) or nitrosoureas;

i) drugs potentially affecting metastasis of tumours such as matrix metalloproteinase inhibitors;

j) gene therapy and antisense agents;

k) antibody therapeutics; and l) other bioactive compounds of marine origin, notably the ecteinascidins such as ecteinascidin 743 and the didemnins such as aplidine.

EXAMPLE

An unidentified sponge (OP-98-18) was collected at Iriomote island, Okinawa on May 1998. The sponge (0.10 kg, wet) was extracted with acetone (0.50 L, 3 times), and the acetone solution was concentrated. The resulting aqueous suspension was partitioned with EtOAc to give 470 mg of lipophilic material (IC50 0.25 µg/mL). Most of it (310 mg) was subjected to chromatographic separation first on silica gel (active fraction, 63.0 mg, eluted with EtOAc-MeOH, 1–1) then preparative TLC (silica, EtOAc-MeOH, 3-1), and finally cation exchange column (eluted with MeOH, and MeOH+0.05% TFA). We obtained totally 10.1 mg (3.2% from extract) of compound 1.

We also found the same compound from another sponge specimen. We initially judged that the sponges were different, however, extracts showed identical 1H NMR spectra of the same species. The original sponge was identified as *Pachastrissa* sp. (Demospongiae, Astrophorida, Calthropellidae). The sponge is deposited both at our lab (voucher no. OP-98-18 and OP-98-21) and at Queensland Museum (QM G317007). The collection was made on May 9, 1998 at Sakiyama Bay, Iriomote Island, Okinawa.

A specimen of the sponge *Pachastrissa* sp. (OP-98-21) was collected. The sponge was brought back to lab and kept frozen until extraction. The sample (0.20 kg, wet) was extracted with acetone (0.5 L, 3 times), and the filtered acetone extract was concentrated. The resulting aqueous suspension was partitioned with EtOAc. The organic layer (1.40 g) showed IC50 0.1 µg/mL. The water layer was concentrated, and the resulting solid material was washed with MeOH. After filtration, MeOH soluble material was taken. This MeOH extract (1.62 g) showed IC50 0.02 µg/mL.

Most (1.4 g) of the MeOH extract was subject to separation, first on Sephadex $LH_{20}$ ($CH_2Cl_2$-MeOH, 1-1), then on HPLC (RP18, not eluted with MeOH-$H_2O$ (19-1), but with EtOAc-MeOH (1-1)), and finally cation exchange column (MeOH, MeOH-0.1% TFA) to give 11.5 mg (0.8 components with MeOH-$H_2O$ first. However, after separation we noticed that we did not recover all the material, so we washed the column with less polar solvent, EtOAc-MeOH. And the compound was recovered in this fraction (checked by NMR and also by cytotoxicity results).

Compound 1 (free form, IK-8-73-4):

white amorphous solid;

$[\alpha]D21+180$ (c 0.1, EtOH);

IR (film) ν max 3342, 2920, 2850, 2355, 1556, 1469, 1215, 1039, 758, 667 cm−1; $^1$H NMR (500 MHz, $CD_3OD$) δ0.90 (3H, m, H-18), 1.29 (24H, brs, H-6 to 17), (2H, m, H-5), 3.43 (1H, dd, J=7.9, 8.9 Hz, H-1), 3.51 (1H, dt, J=4.3, 8.9 Hz, H-2), 3.81 (1H, dt, J=2.8, 6.7 Hz, H-4), 3.86 (1H, dd, J=2.8, 4.3 Hz, H-3), 3.90 (1H, dd, J=7.6, 7.9 Hz, H-1);

$^{13}$C NMR (125 MHz, $CD_3OD$) δ84.3 d (C-4), 73.3 d (C-3), 72.1 t (C-1), 56.0 d (C-2), 33.1 t, 30.9 t (C-5), 30.8 t, 30.7 t, 30.5 t, 30.5 t, 27.1 t, and 23.7 t, (C-6 to C-17), 14.4 q (C-18);

ESIMS m/z 300 ($[M+H]^+$).

Compound 1 (salt form, IK-8-61-4):

white amorphous solid:

$^1$H NMR (500 MHz, $CD_3OD$) δ0.87 (3H, m, H-18), 1.29 (24H, brs, H-6 to 17), 1.65 (2H, m, H-5), 3.71 (1H, dt, J=3.5, 6.6 Hz, H-4), 3.79 (1H, dd, J=5.0, 8.5 Hz, H-1), 3.88 (1H, m, H-2), 3.91 (1H, dd, J=7.3, 8.5 Hz, H-1), 4.25 (1H, dd, J=3.5, 5.2 Hz, H-3);

$^{13}$C NMR (125 MHz, $CD_3OD$) δ84.3 d (C-4), 70.9 d (C-3), 68.9 t (C-1), 54.3 d (C-2), 33.0 t, 30.8 t, 30.7 t, 30.7 t, 30.4 t, 29.7 t (C-5), 27.2 t, and 23.7 t (C-6 to C17), 14.4q (C-18);

EIMS m/z 299 ($M^+$).

What is claimed is:

1. A compound having the formula:

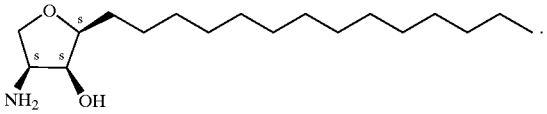

2. A method of treating a tumour which comprises administering an effective amount of a compound of formula:

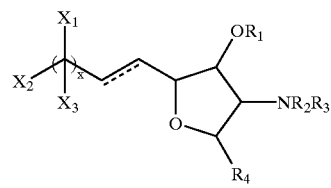

I wherein $R_1$, is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl; or $R_1$ together with $R_2$ or $R_3$ forms a saturated or unsaturated heterocyclic ring: $R_2$ and $R_3$ are each, independently, selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl; or one of $R_2$ or $R_3$ together with $R_1$ forms a saturated or unsaturated heterocyclic ring; or $R_2$ and $R_3$ together form a saturated or unsaturated heterocyclic ring; $R_4$ is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl, wherein R' is selected from the group consisting of H, OH, $NO_2$, $NH_2$, SH, CN, halogen, C(=O)H, C(O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted and unsubstituted aryl; R" is selected from the group consisting of H, OH, $NO_2$, $NH_2$, SH, CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted and unsubstituted aryl;

wherein $X_1$, $X_2$ and $X_3$ on formula I are independently placed in any particular position of the chain and independently selected from H, OH, OR', SH, SR', SOR', $SO_2R'$, $NO_2$, $NH_2$, NHR', $N(R')_2$, NHC(O)R', CN, halogen, =, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic, wherein substituent groups defined by R' are each independently selected from the group consisting of H, OH, OR', SH, SR', SOR', $SO_2R'$, $NO_2$, $NH_2$, NHR', $N(R')_2$, NHC(O)R', CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, and substituted or unsubstituted heteroaromatic; wherein x is 6 to 20 and wherein the dotted line is one or several optional double bonds placed in any particular position of the side chain; or a pharmaceutically acceptable salt thereof.

3. The method of claim 2, wherein the compound is of formula:

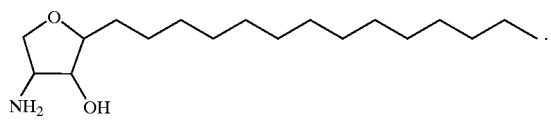

4. A method of preparing compound IK-8-73-4 of structure:

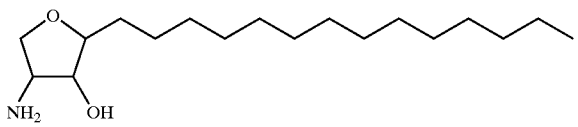

which comprises obtaining a supply of a sponge Pachastrissa sp. containing said compound IK-8-73-4, and extracting the sponge with acetone, thereby isolating IK-8-73-4 from said supply of sponge.

5. A pharmaceutical composition for treatment of a tumour, said composition comprising a compound of formula:

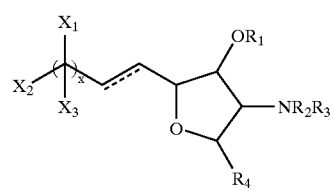

I wherein $R_1$ is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl; or $R_1$ together with $R_2$ or $R_3$ forms a saturated or unsaturated heterocyclic ring; $R_2$ and $R_3$ are each, independently, selected from H, C(=O)R, P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl or substituted or unsubstituted aryl: or one of $R_2$ or $R_3$ together with $R_1$ forms a saturated or unsaturated heterocyclic ring; or $R_2$ and $R_3$ together form a saturated or unsaturated heterocyclic ring; $R_4$ is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl, wherein R' is selected from the group consisting of H, OH, $NO_2$, $NH_2$, SH, CN, halogen, C(=O)H, C(=O)$CH_3$, $CO_2H$, $CO_2CH_3$ substituted or unsubstituted $C_1$–$C_{18}$ alkyl, substituted or unsubstituted $C_2$–$C_{18}$, alkenyl, substituted or unsubstituted $C_2$–$C_{18}$ alkynyl, substituted and unsubstituted aryl; R" is selected from the group consisting of H, OH, $NO_2$, $NH_2$, SH, CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted and unsubstituted aryl;

wherein $X_1$, $X_2$ and $X_3$ on formula I are independently placed in any particular position of the chain and independently selected from H, OH, OR', SH, SR', SOR', $SO_2R'$, $NO_2$, $NH_2$, NHR', $N(R')_2$, NHC(O)R', CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, substituted or unsubstituted heteroaromatic, wherein substituent groups defined by R' are each independently selected from the group consisting of H, OH, OR', SH, SR', SOR', $SO_2R'$, $NO_2$, $NH_2$, NHR', $N(R')_2$, NHC(O)R', CN, halogen, =O, C(=O)H, C(=O)$CH_3$, $CO_2H$, $CO_2CH_3$, substituted or unsubstituted $C_1$–$C_{18}$ alkyl, substituted or unsubstituted $C_2$–$C_{18}$ alkenyl, substituted or unsubstituted $C_2$–$C_{18}$ alkynyl, substituted or unsubstituted aryl, and substituted or unsubstituted heteroaromatic; wherein x is 6 to 20; and wherein the dotted line is one or several optional double bonds placed in any particular position of the side chain; or a pharmaceutically acceptable salt thereof; and a pharmaceutically acceptable carrier.

6. The composition of claim 5, wherein the compound is of formula:

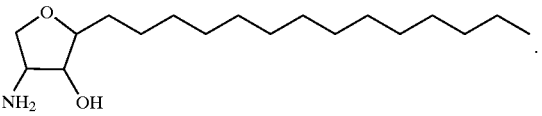

7. The method of claim 2, wherein the compound is:

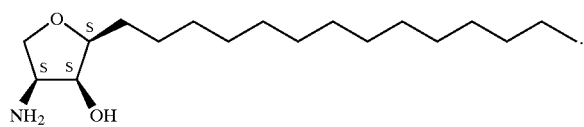

8. The composition of claim 5, wherein the compound is:

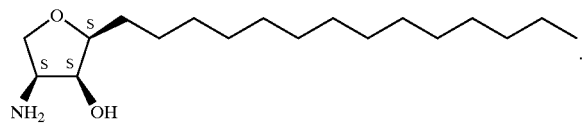

9. The method of claim 2, wherein one of $R_2$ or $R_3$ together with $R_1$ forms a saturated or unsaturated heterocyclic ring and the other is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl.

10. The composition of claim 5, wherein one of $R_2$ or $R_3$ together with $R_1$ forms a saturated or unsaturated heterocyclic ring and the other is selected from H, C(=O)R', P(=O)R'R", S(=O)R'R", substituted or unsubstituted $C_1$–$C_{18}$ alkyl, substituted or unsubstituted $C_2$–$C_{18}$ alkenyl, substituted or unsubstituted $C_2$–$C_{18}$ alkynyl, or substituted or unsubstituted aryl.

* * * * *

UNITED STATES PATENT AND TRADEMARK OFFICE
CERTIFICATE OF CORRECTION

PATENT NO. : 6,864,283 B2
DATED : March 8, 2005
INVENTOR(S) : Tatsuo Higa et al.

It is certified that error appears in the above-identified patent and that said Letters Patent is hereby corrected as shown below:

<u>Column 9,</u>
Line 14, insert -- O -- after "halogen, ="

<u>Column 10,</u>
Line 7, insert -- ' -- after "C(=O)R"

Signed and Sealed this

Nineteenth Day of July, 2005

JON W. DUDAS
*Director of the United States Patent and Trademark Office*